United States Patent [19]
Sakai

[11] Patent Number: 5,907,053
[45] Date of Patent: May 25, 1999

[54] METHOD FOR PREPARING ACRYLONITRILE

[76] Inventor: Katsuhiko Sakai, 1005-1-3-203, Higashitomii, Kurashiki-shi, Okayama 710, Japan

[21] Appl. No.: 08/894,136

[22] PCT Filed: Jan. 25, 1996

[86] PCT No.: PCT/JP96/00133

§ 371 Date: Jul. 30, 1997

§ 102(e) Date: Jul. 30, 1997

[87] PCT Pub. No.: WO96/23765

PCT Pub. Date: Aug. 8, 1996

[30] Foreign Application Priority Data

Jan. 31, 1995 [JP] Japan ................................ 7-032863

[51] Int. Cl.$^6$ ................................................ C07C 255/08
[52] U.S. Cl. ............................................ 558/466; 558/435
[58] Field of Search ...................................... 558/435, 466

[56] References Cited

U.S. PATENT DOCUMENTS 3,649,179 3/1972 Ikeda et al. .
3,661,723 5/1972 Ohashi et al. .

FOREIGN PATENT DOCUMENTS 47-6607 2/1972 Japan .
47-6608 2/1972 Japan .

*Primary Examiner*—Deborah C. Lambkin
*Assistant Examiner*—Ebenezer Sackey

[57] ABSTRACT

This invention relates to a method for preparing acrylonitrile by ammoxydation using a multi-story quenching tower. The method comprises the steps of supplying the reacted gas into the first quenching chamber of the multi-story quenching tower, said first quenching chamber has a water supply pipe equipped with spray nozzles at a two-dimensional density of more than 2 nozzles/m$^2$ for the sectional area of the multi-story quenching tower and contacting the reacted gas with 5 T or more of water per 1 T of the reacted gas fed from the nozzles.

10 Claims, 1 Drawing Sheet

METHOD FOR PREPARING ACRYLONITRILE

This application is a 371 of PCT/JP96/00133 filed Jan. 25, 1996.

TECHNICAL FIELD

The present invention relates to a method for preparing acrylonitrile by ammoxydation, more particularly to a method for improving the yield and production efficiency of acrylonitrile by sufficiently removing ammonia in the quenching process of a reacted gas.

BACKGROUND ART

The method for preparing acrylonitrile by ammoxydation has been improved on various points since its success in industrialization and it is said that the method has technically matured. Still, there have been made efforts to improve utility unit consumption and to reduce production cost by achieving production efficiency.

It is well known that the reacted gas obtained from various raw materials contains by-products such as hydrocyanic acid, acetonitrile or aldehyde in addition to acrylonitrile when acrylonitrile is prepared by ammoxydation. The by-products react with acrylonitrile in the presence of unreacted ammonia or react with one another; as a result, high boiling point compounds are produced. The high boiling point compounds cause not only reduction in the yield of acrylonitrile, the target product, but also clogging at various parts in the quenching tower in the downstream processes. Consequently, the by-products must be immediately separated from the reacted gas. Especially, the unreacted ammonia facilitating undesired reactions must be completely removed as soon as possible.

Conventionally, there has been adopted the method for separating unreacted ammonia in the form of a salt and simultaneously removing other impurities and the by-products mentioned above by preliminarily cooling the reacted gas produced in a reactor, immediately sending the cooled reacted gas to a quenching tower, and washing and quenching the reacted gas with water containing acids such as sulfuric acid. As one of the conventional methods excellent in production efficiency, there has been proposed a method employing a multi-story quenching tower to divide a quenching process into two steps or more, which comprises separating most, unreacted ammonia in the form of a salt by contacting the water containing a sufficient amount of sulfuric acid to neutralize the unreacted ammonia and simultaneously condensing not all but a part of the vapor contained in the reacted gas in the first chamber, and condensing most of the residual vapor in the second chamber (U.S. Pat. No. 3,649,179).

This method succeeded in reducing the cost of recovering and treating the salt because of its higher collectability of ammonia and higher concentration of the resultant ammonium salt than the conventional methods. Yet, the collectability of ammonia achieved by this method is not sufficient. Accordingly, problems such as an acrylonitrile loss and trouble caused by clogging due to high boiling point compounds (so called heavies) have still remained.

DISCLOSURE OF THE INVENTION

The present inventors have made extensive and intensive research to solve the above problems and found that the collectability of ammonia is remarkably enhanced by adjusting the two-dimensional density of spray nozzles and the amount of supplying water in certain ranges. As a result, they achieved the present invention.

This invention provides a method for preparing acrylonitrile by reacting propylene and/or propane, ammonia and molecular oxygen in the presence of a catalyst and purifying the reacted gas in a multi-story quenching tower. The method comprises the steps of supplying the reacted gas into the first quenching chamber of the multi-story quenching tower, said first quenching chamber having a water supply pipe equipped with spray nozzles at a two-dimensional density of 2 nozzles/m$^2$ or more of the cross sectional area of the multi-story quenching tower, and contacting the reacted gas with at least 5 T of water fed from the nozzles per 1 T of the reacted gas. The unit "T" is a measurement of weight and corresponds to 1000 kg.

The quenching tower used in the present invention includes a multi-story quenching tower divided into two or more levels and each level consists of one chamber as shown in FIG. 1.

The gas obtained by reacting propylene and/or propane, ammonia and molecular oxygen is first introduced into the first quenching chamber (2) to cool and wash it by the gas with water containing an acid such as sulfuric acid. At this time, unreacted ammonia, high boiling point compounds, polymers, scattered catalysts and the like are removed. After that, the remaining by-products are removed in the chambers on stories above the first.

In the multi-story quenching tower, spray nozzles (17) are arranged on the end part of a water supply pipe (9). On the upper stories, chambers are filled with porcelain Raschig rings as a packed bed (11).

As the spray nozzles (17), nozzles having the differential pressure of from 1 to 5 kg/cm$^2$G and the spraying angle of from 90 to 100° can be used, for example, hollow cone type and full cone type nozzles. The two-dimensional density of the spray nozzles (17) in the first chamber (2) must be at least 2 nozzles/m$^2$ of the cross sectional area of the multi-story quenching tower. As a result, the areas where each spray nozzle (17) can spray water are preferably overlapped with one another so that excellent collectability of ammonia may be obtained. When the two-dimensional density is less than 2 nozzles/m$^2$, water is not spread all over the cross sectional area of the quenching tower because the sprayed areas are not preferably overlapped. Therefore, the scattered water and the reacted gas are not sufficient contact and the preferable collectability of ammonia is not achieved. The two-dimensional density of the nozzles is preferably from 2 to 8 nozzles/m$^2$, more preferably from 2 to 5 nozzles/m$^2$.

The water supply pipe (9) is arranged above the gas lead in port (19) so that the spray nozzles equipped on the pipe may face the bottom of the chamber. The distance between the port (19) and the spray nozzles 17 is preferably 0.5 m or more, more preferably 1.0 m or more although the distance depends on a diameter of the quenching tower.

Hereinafter, the production method in the present invention will be described by referring to FIG. 1, an example of a multi-story quenching tower. The quenching tower has a diameter of from 2.5 to 3.0 m and a height of from 9 to 10 m. In general, the reacted gas obtained by reacting propylene and/or propane, ammonia and molecular oxygen in the production of acrylonitrile has a composition as follows:

| < ingredient > | < vol. % > |
|---|---|
| acrylonitrile | 6.0–7.0 |
| ammonia | 0.0–1.0 |
| propylene and/or propane | 0.2–0.6 |
| acetonitrile | 0.1–0.5 |
| hydrocyanic acid | 0.8–1.6 |
| non-condensable gas | 60.0–67.0 |
| water vapor | 25.0–30.0 |
| other materials (acrolein, high boiling point compounds, etc.) | 0.0–0.2 |

This gas is supplied to the first quenching chamber (2) through a gas lead in pipe (1) a rate of from at about 15 to 25 T/Hr at a temperature from 260° to 280° C.

In the first chamber (2), water is supplied to the chamber from the spray nozzles (17) in the direction against the flow of the gas at a rate of from 150 to 170 T/Hr. The water contacting the gas may be recycle through a discharging pipe (4) and the water supply pipe (9) into the first quenching chamber again. If necessary, a refrigerator (6) may be used.

The amount of the water supplied to the first chamber (2) must be at least 5 T per 1 T of the reacted gas. If it is less than 5 T per 1 T of the reacted gas, ammonia and high boiling point compounds are not sufficiently collected. As a result, the reacted gas flows up into the above stories and the high boiling point compounds clog the packed bed (11) and pipes. Further, the water is preferably fed in an amount of 20 T or less per 1 T of the reacted gas to obtain desirable collectability of ammonia and utility unit consumption. The more preferable amount of the water is from 7 T to 10 T per 1 T of the reacted gas.

An acid necessary for neutralization of ammonia, preferably sulfuric acid, is added to the water in the first chamber (2). The acid is preferably added so as to adjust the pH value of the water preferably from 5 to 6, more preferably from 5.3 to 5.8. By controlling the pH value within this range, loss of acrylonitrile can be minimized. When the pH value is too high or low, loss of acrylonitrile increases, and moreover, the tower, packed beds, pipes and trays are soiled or clogged in a quenching step and an adsorption step following the quenching step.

Preferably, the reacted gas is supplied to the first chamber (2) at a linear velocity of from 0.10 to 0.90 m/sec. When the linear velocity of the reacted gas is greater than 0.90 m/sec., the collectability of ammonia is likely to be reduced because the reacted gas tends to cause entrainment of water into the later steps. When the linear velocity of the reacted gas is less than 0.10 m/sec., the effects of the present invention are not efficiently attained and the low linear velocity is not preferable in the aspects of initial investment in plant and equipment. The more preferable linear velocity is from 0.50 to 0.80 m/sec.

The reacted gas treated in the first chamber (2) is transferred to the stories above the first (FIG. 1 only shows a two-story quenching tower), and the removal of ammonia in the reacted gas is continued. On the upper stories, the reacted gas can be treated according to the conventional methods.

In the case of the quenching tower shown in FIG. 1, the water in the second chamber (3) is cooled down to a temperature about 36° to 38° C. with a refrigerator (13) and supplied into the second chamber through the water supply pipe (15) at a rate of from 170 to 190 T/Hr. The vapor initially contained in the reacted gas is only partially condensed in the first chamer (2), and most of the vapor is liquefied in this second chamber (3). The water used in the quenching chambers on stories above the first can be recycled in each quenching chamber on stories above the first. If necessary, water containing an acid can be contacted with the reacted gas in the chambers on the upper stories.

The temperature in the first quenching chamber (2), at the time when the inside of the multi-story quenching tower reaches its equilibrium state, is from 80 to 100° C. although it may change somewhat depending on the temperature and composition of the reacted gas transferred into the chamber. When the inside of the quenching tower reaches its equilibrium state, the water in the first quenching chamber (2) becomes a solution containing an extremely small amount of acrylonitrile, ammonium sulfate and viscous high boiling point compounds. The water is discharged from the first quenching chamber (2) out of the tower at a rate of from about 0.5 to 1.0 T/Hr. The pressure at the bottom of the tower is from about 0.4 to 0.6 kg/cm$^2$G.

The reacted gas, from which ammonia is removed in the multi-story quenching tower, is transferred to an absorption tower. The temperature of the gas at the transferring pipe (16) is from about 37° to 39° C.

According to the present invention, collectability of ammonia of 90% or more is achieved and other by-products can be effectively removed while maintaining the original effects of the multi-story quenching tower. Consequently, loss of acrylonitrile and clogging of pipes or packed beds due to the high boiling point compounds can be prevented.

DESCRIPTION OF NUMERALS

Figure 1:
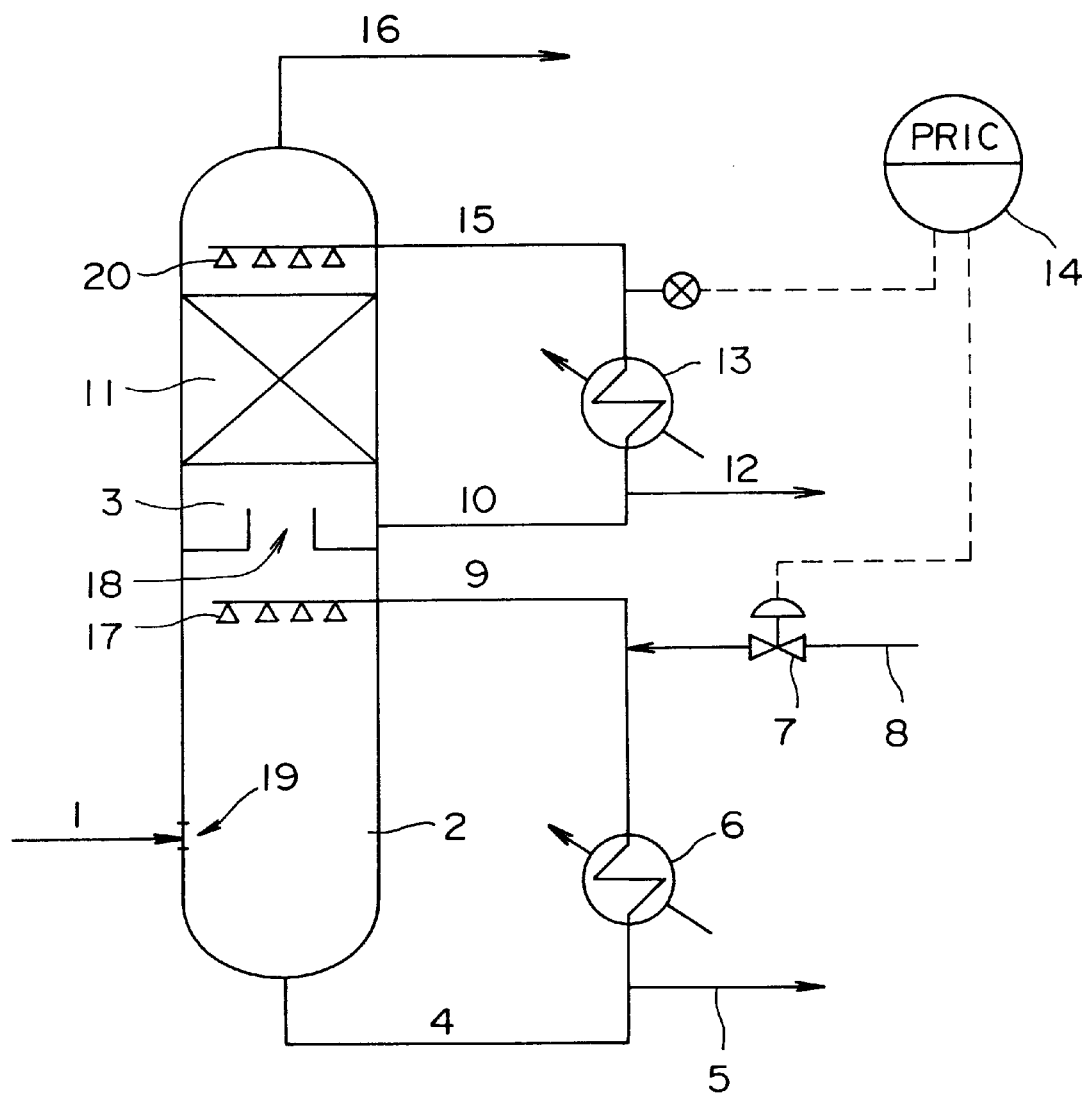
FIG. 1 is a schematic view of the multi-story quenching tower used in the present invention.

1: gas lead in pipe
2: first quenching chamber
3: second quenching chamber
4: water discharging pipe
5: water discharging pipe out of the tower
6: refrigerator
7: acid controlling valve
8: acid supply pipe
9: water supply pipe
10: water discharging pipe
11: packed bed
12: water discharging pipe out of the tower
13: refrigerator
14: pH controlling meter
15: water supply pipe
16: gas transferring pipe
17: spray nozzle
18: gas transferring port
19: gas lead in port
20: spray nozzle

BEST MODE FOR CARRYING OUT THE INVENTION

<EXAMPLE 1>

The multi-story quenching tower disclosed in FIG. 1 was used. The quenching tower had a diameter of 2.7 m and a height of 9.7 m. In the first quenching chamber (2) of the tower, spray nozzles (17) were arranged on the end part of a pipe (9) at the two-dimensional density of 2.3 nozzles/m$^2$ for the sectional area of the quenching tower. The distance from the tip of the nozzle (17) to the gas leading port (19) was 0.5 m. The type of the nozzles was a hollow cone type.

Propylene, ammonia and molecular oxygen were reacted in a reaction tower to obtain a reacted gas with the composition as follows:

| < ingredient > | < vol. % > |
|---|---|
| acrylonitrile | 6.5 |
| ammonia | 0.5 |
| propylene and propane | 0.4 |
| acetonitrile | 0.3 |
| hydrocyanic acid | 1.2 |
| non-condensed gas | 63.5 |
| water vapor | 27.5 |
| other materials (acrolein, high boiling point compounds, etc.) | 0.1 |

The gas was introduced through the gas lead in pipe (1) into the first quenching chamber (2) at 20 T/Hr. The linear velocity of the reacted gas was 0.66 m/sec. The mass plow rate of ammonia contained in this reacted gas was 55 kg/Hr.

Water at a temperature of 85° C., to which sulfuric acid was added so as to adjust the pH value of the water to 5.5, was sprayed from the spray nozzles (17) in an amount of 7.4 T per 1 T of the reacted gas at 148 T/Hr. The water was sprayed all over the section of the first quenching chamber (2).

93% of the ammonia contained in the reacted gas was neutralized and collected in the first quenching chamber (2). The water was discharged out of the tower at 0.8 T/Hr.

The reacted gas treated in the first quenching chamber (2) was transferred to the second quenching chamber (3) through the gas transferring port (18). The packed bed (11) of the second quenching chamber (3) was filled with porcelain Raschig rings and the spray nozzles (20) were equipped in the same manner as in the first chamber (2). Water at temperature of 37° C., whose pH value was adjusted to 5.5 with sulfuric acid, was supplied at 180 T/Hr from the spray nozzles (20).

The 7% of the ammonia remaining in the reacted gas was completely collected in the second chamber (3); therefore, the gas exhausted through the transferring pipe (16) did not contain ammonia. When the system in the tower reached its equilibrium state, the pressure at the bottom of the tower was 0.5 kg/cm$^2$G.

<Comparative Example 1>

The reacted gas with the composition shown in Example 1 was purified in the same manner as in Example 1 except that the two-dimensional density of the nozzles was 3.7 nozzles/m$^2$ and the amount of water supplied to the first chamber was 3.9 T per 1 T of the reacted gas. Only 77% of the ammonia was removed from the reacted gas, ie, the ammonia level in transferring pipe (16) was 23% of the ammonia level in lead-in pipe (1).

<Comparative Example 2>

The reacted gas with the composition shown in Example 1 was purified in the same manner as in Example 1 except that the two-dimensional density of the nozzles was 1.9 nozzles/m$^2$. Only 88% of the ammonia was removed from the reacted gas, ie, the ammonia level in transferring pipe (16) was 12% of the ammonia level in lead-in pipe (1).

INDUSTRIAL APPLICATION

According to the method of the present invention, collectability of ammonia is improved so that the yield of acrylonitrile can be increased and trouble, such as clogging in the tower due to the high boiling point compounds, is avoided.

What is claimed is:

1. A method for preparing acrylonitrile in the presence of a catalyst comprising: reacting ammonia, molecular oxygen and at least one reactant chosen from the group consisting of propylene and propane to form a reacted gas; and purifying the reacted gas in a multi-story quenching tower by supplying the reacted gas into a first quenching chamber of the quenching tower, wherein said first quenching chamber comprises a water supply pipe equipped with nozzles at a two-dimensional density of at least 2 nozzles/m$^2$ of the cross-sectional area of the quenching tower, and contacting the reacted gas with at least 5000 Kg of water fed from the nozzles per 1000 Kg of the reacted gas.

2. The method for preparing acrylonitrile according to claim 1, wherein the reacted gas is supplied at a linear velocity of from 0.1 m/sec to 0.9 m/sec into said first quenching chamber.

3. The method for preparing acrylonitrile according to claim 1, wherein at least one spray nozzle is selected from the group consisting of a full cone type nozzle and a hollow cone type nozzle.

4. The method for preparing acrylonitrile according to claim 1, wherein the density of nozzles is from 2 to 8 nozzles/m$^2$.

5. The method for preparing acrylonitrile according to claim 4, wherein the density of nozzles is from 2 to 5 nozzles/m$^2$.

6. The method for preparing acrylonitrile according to claim 1, wherein from 5000 Kg to 20,000 Kg of water is fed from the nozzles per 1000 Kg of the reacted gas.

7. The method for preparing acrylonitrile according to claim 1, wherein the reacted gas is supplied to the first quenching chamber by a gas lead-in port (19) and wherein the distance between the spray nozzles (17) and the gas lead-in port (19) is 0.5 meters or more.

8. The method for preparing acrylonitrile according to claim 7, wherein the distance between the spray nozzles (17) and the gas lead-in port (19) is 1.0 meters or more.

9. The method for preparing acrylonitrile according to claim 1, wherein the reacted gas is supplied to the first quenching chamber at a linear velocity of from 0.10 to 0.90 m/sec.

10. The method for preparing acrylonitrile according to claim 9, wherein the reacted gas is supplied to the first quenching chamber at a linear velocity of from 0.50 to 0.80 m/sec.

* * * * *

UNITED STATES PATENT AND TRADEMARK OFFICE
CERTIFICATE OF CORRECTION

PATENT NO.   :   5,907,053

DATED        :   May 25, 1999

INVENTOR(S   :   Sakai

It is certified that error appears in the above-identified patent and that said Letters Patent is hereby corrected as shown below:

Front page, below item [76] add --item [73] Assignee: ASAHI KASEI KOGYO KABUSHIKI KAISHA, Osaka, Japan--.

In column 2, line 25, "by the gas" should be change to --by contacting the gas--.

In column 2, line 57, "nozzles 17" should be changed to --nozzles (17)--.

In column 3, line 14, "lead in pipe (1) a rate" should be changed to --lead-in pipe (1) at a rate--.

In column 4, line 36, "gas lead in pipe" should be changed to --gas lead-in pipe--.

In column 4, line 57, "gas lead in port" should be changed to --gas lead-in port--.

In column 5, line 3, "gas leading port" should be changed to --gas lead-in port--.

In column 5, line 21, "gas lead in pipe" should be changed to --gas lead-in pipe--.

In column 5, line 23, "mass plow" should be changed to --mass flow--.

Signed and Sealed this

Eleventh Day of April, 2000

Attest:

Q. TODD DICKINSON

*Attesting Officer*                *Director of Patents and Trademarks*